(12) United States Patent
Malkowski

(10) Patent No.: US 9,510,823 B2
(45) Date of Patent: Dec. 6, 2016

(54) DEVICES, SYSTEMS, AND METHODS FOR WOUND CLOSURE

(71) Applicant: COVIDIEN LP, Mansfield, MA (US)

(72) Inventor: Jaroslaw T. Malkowski, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 368 days.

(21) Appl. No.: 14/173,123

(22) Filed: Feb. 5, 2014

(65) Prior Publication Data

US 2015/0038995 A1 Feb. 5, 2015

Related U.S. Application Data

(60) Provisional application No. 61/861,732, filed on Aug. 2, 2013.

(51) Int. Cl.
| | | |
|---|---|---|
| *A61B 17/04* | (2006.01) | |
| *A61B 17/00* | (2006.01) | |
| *A61B 17/06* | (2006.01) | |

(52) U.S. Cl.
CPC ....... *A61B 17/0482* (2013.01); *A61B 17/0057* (2013.01); *A61B 2017/00637* (2013.01); *A61B 2017/00663* (2013.01); *A61B 2017/06052* (2013.01)

(58) Field of Classification Search
CPC ............ A61B 17/0482; A61B 17/0469; A61B 17/0057; A61B 2017/00637; A61B 2017/00663; A61B 2017/06052; A61B 17/0485

USPC .......................................................... 606/148
See application file for complete search history.

(56) References Cited

U.S. PATENT DOCUMENTS

| | | |
|---|---|---|
| 5,222,508 A | 6/1993 | Contarini |
| 5,374,275 A | 12/1994 | Bradley et al. |
| 5,439,469 A | 8/1995 | Heaven et al. |
| 5,476,470 A | 12/1995 | Fitzgibbons, Jr. |
| 5,478,344 A | 12/1995 | Stone et al. |
| 5,507,758 A | 4/1996 | Thomason et al. |
| 5,562,688 A | 10/1996 | Riza |
| 5,984,948 A | 11/1999 | Hasson |
| 6,203,554 B1 | 3/2001 | Roberts |
| 6,551,329 B1 | 4/2003 | Kortenbach et al. |
| 6,562,052 B2 | 5/2003 | Nobles et al. |
| 7,160,309 B2 | 1/2007 | Voss |
| 8,007,512 B2 | 8/2011 | Ginn et al. |
| 8,202,281 B2 | 6/2012 | Voss |
| 2002/0065524 A1 | 5/2002 | Miller et al. |
| 2006/0030868 A1 | 2/2006 | Bennett |

(Continued)

*Primary Examiner* — Katrina Stransky

(57) ABSTRACT

A wound closure device includes outer and inner members. The inner member is configured for receipt of a suture passer and is pivotably coupled to the outer member. The inner member is pivotable relative to the outer member between a first position, wherein the inner member is coaxially disposed relative to the outer member, a second position, wherein the distal end of the inner member extends outwardly from the outer member in a first direction and the proximal end of the inner member extends outwardly from the outer member in a second, opposite direction, and a third position, wherein the distal end of the inner member extends outwardly from the outer member in the second direction and the proximal end of the inner member extends outwardly from the outer member in the first direction.

14 Claims, 7 Drawing Sheets

(56) References Cited

U.S. PATENT DOCUMENTS

| | | |
|---|---|---|
| 2006/0142784 A1 | 6/2006 | Kontos |
| 2006/0276871 A1* | 12/2006 | Lamson .................... A61F 2/82 623/1.11 |
| 2008/0269786 A1* | 10/2008 | Nobles ............... A61B 17/0057 606/145 |
| 2010/0185217 A1 | 7/2010 | Hsu et al. |
| 2010/0234860 A1 | 9/2010 | Chambers |
| 2010/0249808 A1 | 9/2010 | Harada et al. |
| 2010/0262166 A1 | 10/2010 | Boraiah et al. |
| 2011/0082473 A1 | 4/2011 | Smith |
| 2011/0082475 A1 | 4/2011 | Smith |
| 2011/0082477 A1 | 4/2011 | Smith |
| 2011/0112553 A1 | 5/2011 | Smith |
| 2011/0112557 A1 | 5/2011 | Beeley |
| 2011/0313433 A1* | 12/2011 | Woodard, Jr. ..... A61B 17/0469 606/145 |
| 2012/0029532 A1 | 2/2012 | Hodgkinson et al. |
| 2012/0245599 A1 | 9/2012 | Abbott et al. |
| 2012/0265223 A1 | 10/2012 | Shpaichler et al. |
| 2012/0316579 A1 | 12/2012 | Ma |
| 2013/0012962 A1 | 1/2013 | Stone |

* cited by examiner

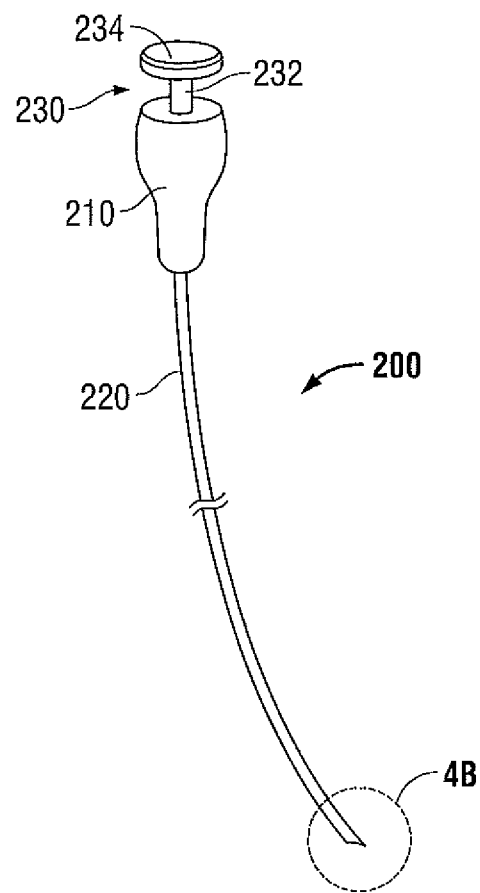
FIG. 4A
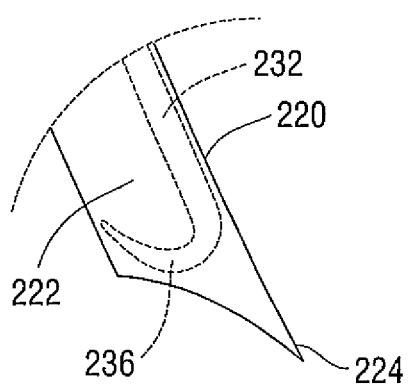
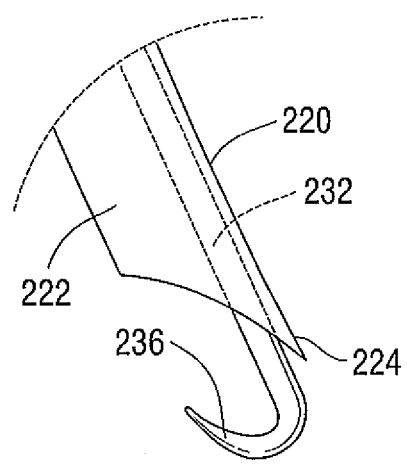
FIG. 4B  FIG. 4C

DEVICES, SYSTEMS, AND METHODS FOR WOUND CLOSURE

CROSS-REFERENCE TO RELATED APPLICATION

This application claims the benefit of and priority to U.S. Provisional Patent Application No. 61/861,732, filed on Aug. 2, 2013, the entire contents of which are hereby incorporated by reference herein.

BACKGROUND

Technical Field

The present disclosure relates to wound closure and, more particularly, to devices, systems, and methods for closing a wound or opening in tissue.

Background of Related Art

Puncture wounds, wounds that pierce through tissue, may result from trauma or may be intentionally created in order to provide access to a body cavity during surgical procedures. During endoscopic surgical procedures, for example, a trocar device is utilized to puncture the peritoneum to provide access by way of a cannula through the abdominal wall. Generally, a cannula or other access device is placed through the abdominal wall for introduction of surgical instrumentation which is necessary to carry out the surgical procedure. In this manner, the surgeon may introduce a surgical instrument such as a forceps, scissor, clip applier, stapler or any other surgical instrument which may be necessary during the particular surgical procedure. Once the procedure is complete, it is necessary to close the wound.

SUMMARY

A wound closure device is provided that facilitates insertion of a suture through tissue on opposite side of the opening to facilitate tying off of the suture to close the opening in tissue.

In accordance with the present disclosure, a wound closure device is provided generally including an outer member and an inner member. The outer member defines a proximal end and a distal end. The inner member is at least partially disposed within the outer member and defines a proximal end and a distal end. The inner member is configured for receipt of a suture passer therethrough. The inner member is pivotably coupled to the outer member at an intermediate position between the proximal and distal ends of both the outer member and the inner member. The inner member is pivotable relative to the outer member between a first position, wherein the inner member is coaxially disposed relative to the outer member, a second position, wherein the inner member is pivoted relative to the outer member such that the distal end of the inner member extends radially outwardly from the outer member in a first direction and such that the proximal end of the inner member extends radially outwardly from the outer member in a second, opposite direction, and a third position, wherein the inner member is pivoted relative to the outer member such that the distal end of the inner member extends radially outwardly from the outer member in the second direction and such that the proximal end of the inner member extends radially outwardly from the outer member in the first direction.

In aspects of the present disclosure, in the first position, the inner member is disposed within an outer radial dimension of the outer member.

In aspects of the present disclosure, the outer member includes a handle portion disposed at the proximal end thereof, a distal cap disposed at the distal end thereof, and a body portion extending between the handle portion and distal cap. The distal cap may define an atraumatic distal tip. The handle portion may be disposed within an outer radial dimension of the distal cap and/or the body portion.

In aspects, the outer member includes a pair of opposed side walls configured to receive the inner member therebetween.

In aspects, a pivot pin pivotably couples the side walls of the outer member to the inner member.

In aspects, each side wall defines at least one cut-out configured to facilitate pivoting of the inner member relative to the outer member from the first position to one of the second and/or third positions.

In aspects, the inner member defines first and second lumens extending longitudinally therethrough on opposite sides thereof. The first lumen is configured to guide a suture passer through tissue when the inner member is disposed in the first deployed position. The second lumen is configured to guide a suture passer through tissue when the inner member is disposed in the second deployed position. The suture passer lumens may define curved configurations, linear configurations, or combinations thereof.

A method of closing an opening in tissue provided in accordance with the present disclosure includes positioning a wound closure device within an opening in tissue. The wound closure device includes an outer member and an inner member at least partially disposed within the outer member and pivotably coupled to the outer member. The wound closure device may further be configured to include any of the aspects detailed above. The method further includes pivoting the inner member relative to the outer member from a first position, wherein the inner member is coaxially disposed relative to the outer member, to a second position, wherein the inner member is pivoted relative to the outer member such that a distal end of the inner member extends radially outwardly from the outer member adjacent tissue on a first side of the opening in tissue, and such that a proximal end of the inner member extends radially outwardly from the outer member in an opposite direction; inserting a suture passer through the inner member, through tissue, and into an internal surgical site on the first side of the opening in tissue to at least one of deposit and retrieve a portion of a suture; withdrawing the suture passer proximally through tissue and the inner member; pivoting the inner member relative to the outer member from the second position to a third position, wherein the inner member is pivoted relative to the outer member such that the distal end of the inner member extends radially outwardly from the outer member adjacent tissue on a second, opposite side of the opening in tissue, and such that the proximal end of the inner member extends radially outwardly from the outer member in an opposite direction; inserting the suture passer through the inner member, through tissue, and into an internal surgical site on the second side of the opening in tissue to at least one of deposit and retrieve the portion of a suture; and withdrawing the suture passer proximally through tissue and the inner member.

In aspects, the method initially includes providing a surgical access assembly disposed within an opening in tissue; inserting the wound closure device through the surgical access assembly; and withdrawing the surgical access assembly from the opening in tissue, proximally about the wound closure device such that the wound closure device is left positioned within the opening in tissue.

In aspects, the method further includes before inserting the suture passer into the internal surgical site on the first side of the opening in tissue, engaging the portion of suture with the suture passer such that, upon insertion of the suture passer, the portion of suture is translated distally through the inner member and tissue into the internal surgical site; and depositing the portion of suture within the internal surgical site once the portion of suture is positioned within the internal surgical site.

In aspects, the method further includes, after inserting the suture passer into the internal surgical site on the second side of the opening in tissue, engaging the portion of suture with the suture passer, such that, upon withdrawal of the suture passer, the portion of suture is likewise withdrawn proximally though tissue and the inner member.

In aspects, the method further includes tying off the suture to close the opening in tissue.

BRIEF DESCRIPTION OF THE DRAWINGS

Various aspects and features of the presently disclosure are described hereinbelow with references to the drawings, wherein:

FIG. 4A is a perspective view of a suture passer configured for use with the wound closure device of FIG. 1A;

FIG. 4B is an enlarged view of the area of detail indicated as "4B" in FIG. 4A, showing the suture passer disposed in a retracted position;

FIG. 4C is an enlarged view of the distal end of the suture passer of FIG. 4A, showing the suture passer disposed in an extended position;

DETAILED DESCRIPTION OF THE EMBODIMENTS

Figure 1A:
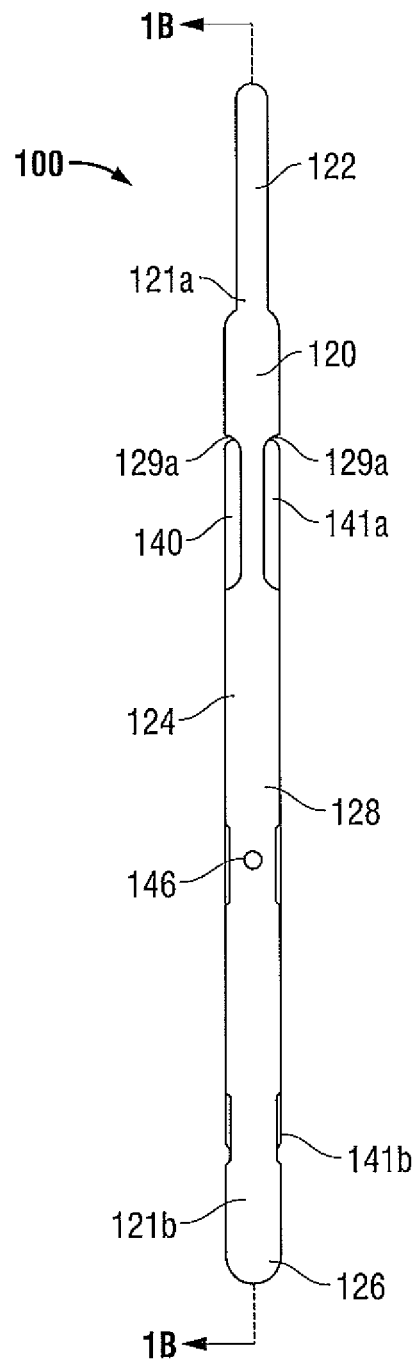
FIG. 1A is a side view of a wound closure device provided in accordance with the present disclosure, shown disposed in an insertion/withdrawal position.

In the figures and in the description that follows, in which like reference numerals identify similar or identical elements, the term "proximal" will refer to the end of the apparatus or portion thereof which is closest to the operator during use, while the term "distal" will refer to the end or portion which is farthest from the operator, as is traditional.

Turning to FIGS. 1A-3, a wound closure device provided in accordance with the present disclosure is shown generally as wound closure device 100. Wound closure device 100 includes an outer member 120 and an inner member 140. Outer member 120 defines a proximal end 121a and a distal end 121b and includes a handle portion 122, a body portion 124, and a distal cap 126. Handle portion 122 is defined at proximal end 121a of outer member 120, distal cap 126 is defined at distal end 121b of outer member 120, and body portion 124 extends between and interconnects handle portion 122 and distal cap 126. Handle portion 122 is fully disposed within the outer radial dimension of outer member 120, as defined by body portion 124 and/or distal cap 126. In use, outer member 120 is configured for insertion partially through an opening in tissue such that distal cap 126 is disposed within the internal surgical site, handle portion 122 remains external or proximal of the opening in tissue, and body portion 124 extends through the opening in tissue. Handle portion 122 facilitates the grasping and manipulating of wound closure device 100. Distal cap 126 encloses distal end 121b of outer member 120 and defines an atraumatic configuration to facilitate insertion through a surgical access assembly, e.g., surgical access assembly 300 (FIG. 5A), and/or manipulation of wound closure device 100 relative to tissue without damage.

Body portion 124 of outer member 120 is generally hollow and cylindrical in configuration, includes a pair of opposed side walls 128, and defines an elongated longitudinal passage 130 partially enclosed by opposed side walls 128. A slot 132 (FIG. 1B) is defined within body portion 124 between side walls 128, thus providing access to passage 130 from the exterior of body portion 124 on opposing sides thereof. Each side wall 128 defines a pair of cut-outs 129a positioned towards the proximal end thereof. As such, the width of slot 132 (FIG. 1B) is enlarged in the vicinity of cut-outs 129a (see FIG. 1A). Each side wall 128 further defines an opposed aperture 129b intermediately disposed between the proximal and distal ends thereof.

Figure 1B:
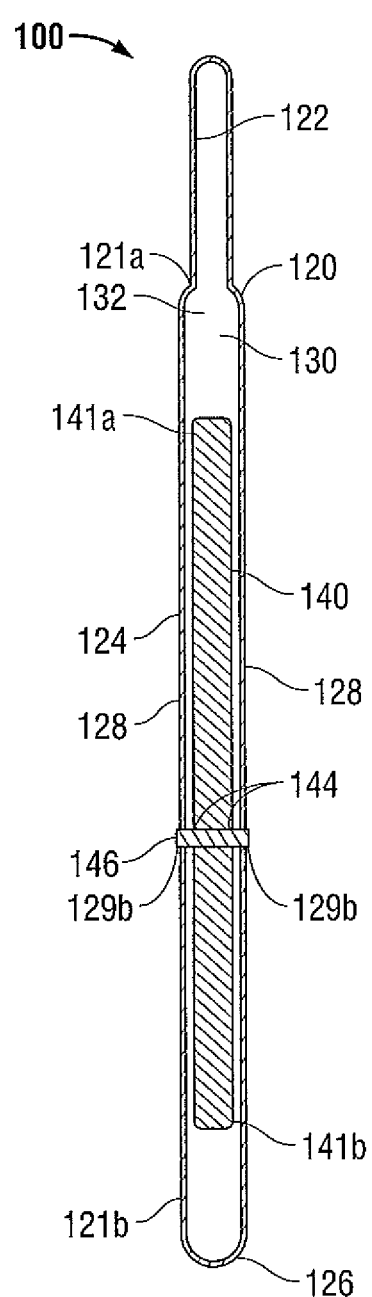
FIG. 1B is a longitudinal, cross-sectional view of the wound closure device of FIG. 1A taken along section line "1B-1B" in FIG. 1A.
Figure 2:
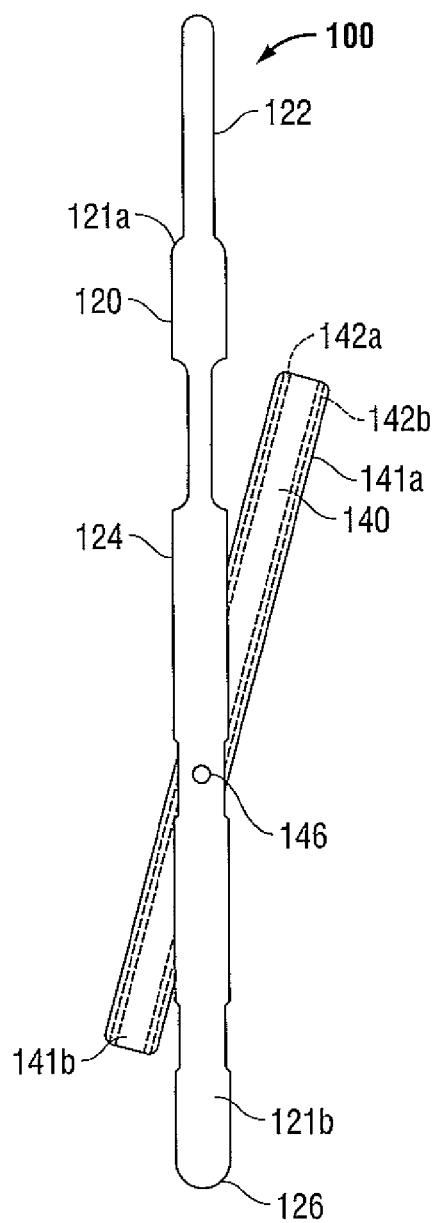
FIG. 2 is a side view of the wound closure device of FIG. 1A, shown disposed in a first deployed position.
Figure 3:
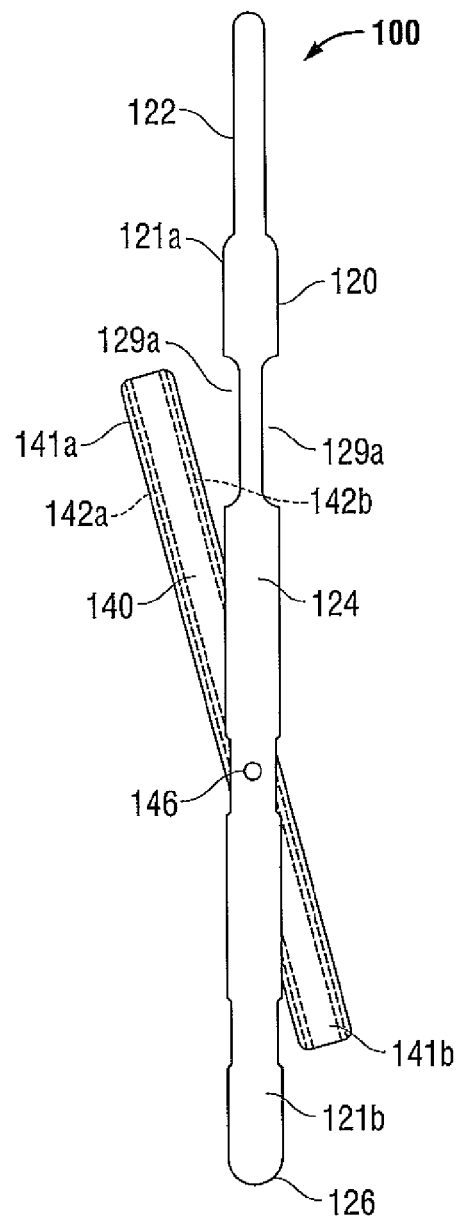
FIG. 3 is a side view of the wound closure device of FIG. 1A, shown disposed in a second deployed position.

Continuing with reference to FIGS. 1A-3, inner member 140 of wound closure device 100 defines a generally cylindrical configuration having a proximal end 141a, a distal end 141b, and including first and second lumens 142a, 142b (FIGS. 2-3) extending longitudinally therethrough on opposite sides of inner member 140. Inner member 140 is dimensioned similar to but slightly smaller than body portion 124 of outer member 120 and is configured for positioning within passage 130 of body portion 124. Inner member 140 defines a pair of opposed apertures 144 intermediately disposed between the proximal and distal ends thereof. Apertures 144 are aligned with respective opposed apertures 129b of body portion 124 of outer member 120 and, as such, pivot pin 146 (see FIG. 1B) extends through the respective first and second pairs of aligned apertures 129b, 144 to pivotably couple outer and inner members 120, 140 to one another. Lumens 142a, 142b (FIGS. 2-3) are disposed on opposite sides of pivot pin 146, e.g., in front and behind pivot pin 146, such that pivot pin 146 does not interfere with lumens 142a, 142b (FIGS. 2-3).

Inner member 140 is manually pivotable relative to outer member 120 between an insertion/withdrawal position, a first deployed position, and a second deployed position. In the insertion/withdrawal position, inner member 140 is coaxially disposed within outer member 120 such that inner member 140 does not extend beyond the outer radial dimension of body portion 124 of outer member 120 (FIGS. 1A and 1B). In the first deployed position, inner member 140 is pivoted relative to outer member 120 about pivot pin 146 such that proximal end 141a of inner member 140 extends radially outwardly from body 124 of outer member 120 in a first direction and distal end 141b of inner member 140 extends radially outwardly from body 124 of outer member 120 in a second, opposite direction (FIG. 2). In the second deployed position, inner member 140 is pivoted relative to outer member 120 about pivot pin 146 such that proximal end 141a of inner member 140 extends radially outwardly from body 124 of outer member 120 in the second direction and distal end 141b of inner member 140 extends radially outwardly from body 124 of outer member 120 in the first direction (FIG. 3). As will be detailed below, cut-outs 129a of side walls 128 of body portion 124 of outer member 120 facilitate the manual urging of inner member 140 from the insertion/withdrawal position to the first and second deployed positions.

Referring to FIGS. 4A-4C, a suture passer provided in accordance with the present disclosure and configured for use with wound closure device 100 (FIGS. 1A-3) is shown generally as suture passer 200, although any other suitable suture passer may be used in conjunction with wound closure device 100 (FIGS. 1A-3). Suture passer 200 includes a handle portion 210, an elongated hollow needle 220 extending distally from handle portion 210, and a plunger 230 slidably disposed within handle portion 210 and needle 220. Handle portion 210 is ergonomically configured to facilitate grasping of suture passer 200 and defines a longitudinal passageway (not shown) extending therethrough. Needle 220 is fixedly engaged to and extends distally from handle portion 210. Needle 220 defines a longitudinal lumen 222 in communication with the longitudinal passageway (not shown) of handle portion 210. Needle 220 further defines a distal tip 224 that may be pointed or otherwise configured to facilitate penetration through tissue. Needle 220 may define a curved configuration (as shown) or may define a linear configuration. Further needle 220 may be substantially flexible or substantially rigid, depending on a particular purpose.

Plunger 230 of suture passer 200 includes an elongated shaft 232 extending through the passageway (not shown) of handle portion 210 and longitudinal lumen 222 of needle 220. An actuator 234 is disposed at the proximal end of shaft 232, extending proximally from handle portion 210. Shaft 232 may define a "J" or hook-shaped distal end 236 to facilitate retrieval of a portion of suture "S" (FIG. 5D), although other configurations are also contemplated. Plunger 230 is selectively translatable, upon depression of actuator 234, through the passageway (not shown) of handle portion 210 and longitudinal lumen 222 of needle 220 from a retracted position, wherein shaft 232 does not extend distally from needle 220 (FIG. 4B), to an extended position, wherein hooked distal end 236 of shaft 232 extends distally from needle 220 (FIG. 4C). A biasing member (not shown) may be provided for biasing shaft 232 of plunger 230 towards the retracted position.

Figure 5A:
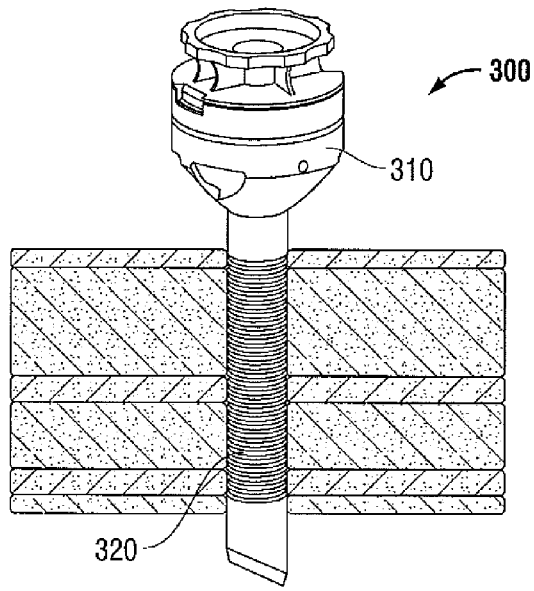
FIG. 5A is a side, perspective, partial cross-sectional view of a surgical access assembly configured for use with the wound closure device of FIG. 1A, shown positioned within an opening in tissue.

Turning now to FIG. 5A, an exemplary surgical access assembly configured for use with wound closure device 100 (FIGS. 1A-3) is shown designated as surgical access assembly 300. Surgical access assembly 300 generally includes a proximal housing 310 and an elongated body 320 extending distally from proximal housing 310. Surgical access assembly 300 is configured for insertion into an opening in tissue such that proximal housing 310 is positioned proximally adjacent the opening, while elongated body 320 extends distally though the opening and into the internal body cavity. Surgical access assembly 300 may include an inflation port (not shown) and one or more seal members (not shown) configured to facilitate insufflation of the internal body cavity and to maintain the internal body cavity in an insufflated state during use, e.g., during insertion, manipulation, and/or withdrawal of surgical instrumentation through access assembly 300. Any other suitable surgical access assembly may likewise be provided for use in accordance with the present disclosure.

With reference to FIGS. 5A-5G, the use and operation of wound closure device 100, in conjunction with suture passer 200 and surgical access assembly 300, for closing an opening in tissue is described. As mentioned above, surgical access assembly 300 is typically utilized during a minimally-invasive surgical procedure to maintain the internal body cavity in an insufflated state during use and/or to facilitate the insertion, manipulation, and/or withdrawal of surgical instrumentation through access assembly 300 during the course of the surgical procedure. Once the procedure is complete and the surgical instrumentation has been withdrawn from access assembly 300, access assembly 300 is maintained within the opening in tissue, as shown in FIG. 5A.

Figure 5B:
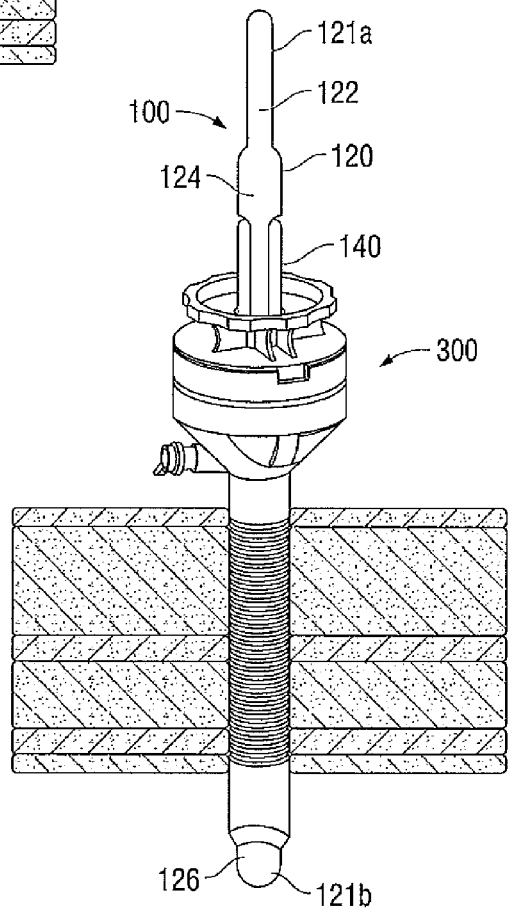
FIG. 5B is a side, perspective, partial cross-sectional view illustrating the wound closure device of FIG. 1A inserted through the surgical access assembly of FIG. 5A and disposed in the insertion/withdrawal position.
Figure 5C:
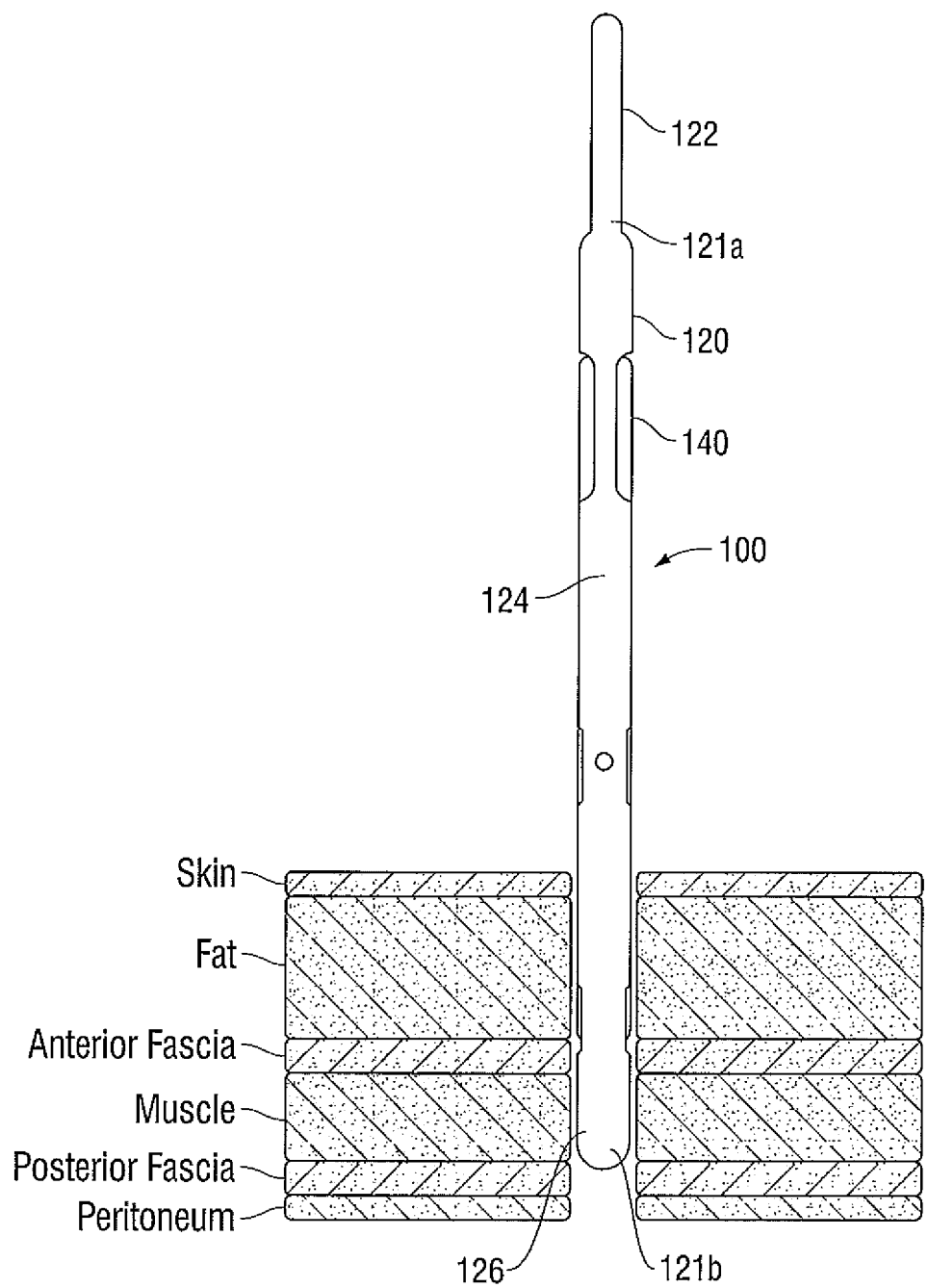
FIG. 5C is a side, perspective, partial cross-sectional view illustrating the wound closure device of FIG. 1A positioned within the opening in tissue in the insertion/withdrawal position, after withdrawal of the surgical access assembly from the opening in tissue.

Referring to FIGS. 5B-5C, to close the opening in tissue, wound closure device 100 is first inserted into through access assembly 300 with inner member 140 disposed in the insertion/withdrawal position. More specifically, with wound closure device 100 defining a low-profile configuration as a result of inner member 140 being disposed in the insertion/withdrawal position, wound closure device 100 is inserted through access assembly 300 such that distal end 121b of outer member 120 of wound closure device 100 extends distally from access assembly 300 into the internal surgical site, while proximal end 121a of outer member 120 of wound closure device 100 remains proximally disposed relative to access assembly 300. Once wound closure device 100 has been inserted through access assembly 300, as shown in FIG. 5B, access assembly 300 is withdrawn from the opening in tissue about wound closure device 100, leaving wound closure device 100 disposed within the opening in tissue as shown in FIG. 5C. More specifically, as wound closure device 100 defines a low profile configuration substantially along its length when disposed in the insertion/withdrawal position, withdrawal of access assembly 300 about wound closure device 100 can be readily effected. Alternatively, wound closure device 100 may be inserted through the opening in tissue after withdrawal of the access assembly 300.

Figure 5D:
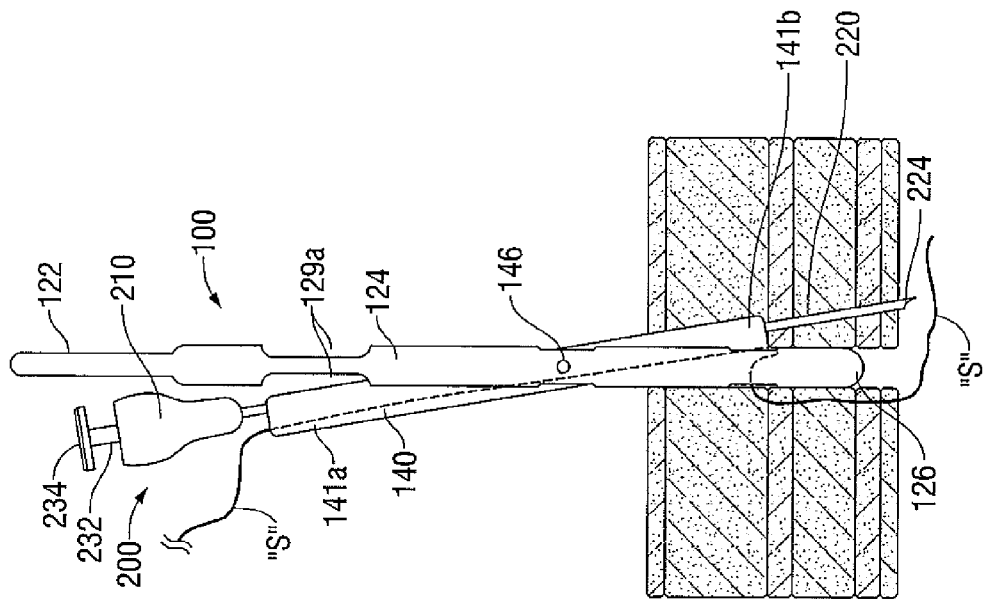
FIG. 5D is a side, perspective, partial cross-sectional view of the wound closure device of FIG. 1A positioned within the opening in tissue in the first deployed position and including the suture passer of FIG. 4A extending therethrough for depositing a portion of suture within an internal surgical site.

With reference to FIG. 5D, once access assembly 300 (FIGS. 5A-5B) has been withdrawn, inner member 140 of wound closure device 100 is transitioned from the insertion/withdrawal position to the first deployed position, wherein inner member 140 is pivoted relative to outer member 120 about pivot pin 146 such that proximal end 141*a* of inner member 140 extends radially outwardly from body 124 of outer member 120 in the first direction and distal end 141*b* of inner member 140 extends radially outwardly from body 124 of outer member 120 in the second, opposite direction. As mentioned above, cut-outs 129*a* of side walls 128 of body portion 124 of outer member 120 facilitate the pivoting of inner member 140 from the insertion/withdrawal position to the deployed positions. That is, cut-outs 129*a* allow the user to urge proximal end 141*a* of inner member relative to outer member 120 without requiring the user to extend a finger (or tool) between side walls 128 (FIGS. 1A-3).

In the first deployed position, as shown in FIG. 5D, distal end 141*b* of inner member 140 is angled towards tissue adjacent the opening in tissue. The particular angled position of distal end 141*b* of inner member 140 relative to tissue may depend on the procedure being performed, the location of the opening in tissue, the patient's anatomy, the user's preference, and/or other factors. For some procedures, it has been found that positioning distal end 141*b* of inner member 140 distally of the skin and fatty layer of tissue and such that distal end 141*b* is positioned proximally adjacent the fascia and muscle layers of tissue is advantageous in that fascia and muscle layers are better suited to receive and retain a suture "S" (FIG. 5D) for closing the opening in tissue (see FIG. 5A, which labels the various tissue layers of the abdominal wall, for example).

With inner member 140 disposed in the first deployed position, or prior thereto, suture passer 200 is prepped for use. More specifically, with reference to FIGS. 4A-4C, shaft 232 of suture passer 200 is transitioned to the extended position, e.g., via depressing actuator 234, such that hooked distal end 236 of shaft 232 extends distally from needle 220. A portion of suture "S" (FIG. 5D) is then positioned within the saddle of hooked distal end 236. Thereafter, shaft 232 is returned to the retracted position, e.g., via releasing or otherwise returning actuator 234 to its initial position, to retain the portion of suture "S" (FIG. 5D) at the distal end of suture passer 200.

Referring again to FIG. 5D, once suture passer 200 has been prepped as detailed above, suture passer 200, lead by distal tip 224 of needle 220, is inserted through one of the lumens, e.g., lumen 142*a* (FIGS. 2-3), of inner member 140, through tissue, and into the internal surgical site. As can be appreciated, with the portion of suture "S" retained at the distal end of suture passer 200, the portion of suture "S" is likewise translated through lumen 142*a* (FIGS. 2-3) of inner member 140, distally through tissue, and into the surgical site. Thereafter, the portion of suture "S" is disengaged from suture passer 200 and deposited within the internal surgical site. More specifically, in order to deposit the portion of suture "S," actuator 234 is depressed, returning shaft 232 to the extended position such that the portion of suture "S" may be removed from the saddle of hooked distal end 236 of shaft 232 (see FIGS. 4A-4C), e.g., via manipulating suture passer 200 relative to the portion of suture "S." Once the portion of suture "S" has been released, suture passer 200 may be returned to the retracted position and withdrawn proximally through tissue and lumen 142*a* (FIGS. 2-3) of inner member 140, leaving the portion of suture "S" extending through tissue.

Figure 5E:
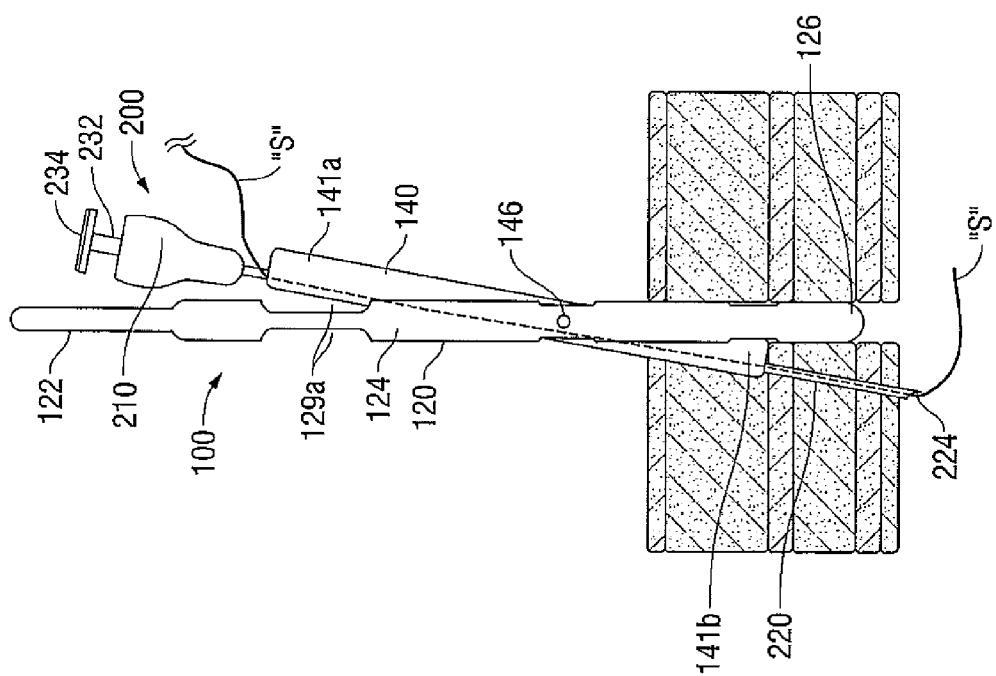
FIG. 5E is a side, perspective, partial cross-sectional view of the wound closure device of FIG. 1A positioned within the opening in tissue in the second deployed position and including the suture passer of FIG. 4A extending therethrough for retrieving the portion of suture from the internal surgical site.

Turning to FIG. 5E, once suture passer 200 has been withdrawn, wound closure device 100 is transitioned from the first deployed position to the second deployed position, wherein inner member 140 is pivoted relative to outer member 120 about pivot pin 146 such that proximal end 141*a* of inner member 140 extends radially outwardly from body 124 of outer member 120 in the second direction and distal end 141*b* of inner member 140 extends radially outwardly from body 124 of outer member 120 in the first direction. That is, in the second deployed position, distal end 141*b* of inner member 140 is angled towards tissue adjacent the opening in tissue on the opposite side of the opening as compared to the first deployed position.

With inner member 140 disposed in the second deployed position, suture passer 200, lead by distal tip 224 of needle 220, is inserted through the other lumen, e.g., lumen 142*b* (FIGS. 2-3), of inner member 140, through tissue, and into the internal surgical site, as shown in FIG. 5E. Once positioned within the internal surgical site, the portion of suture "S" may be retrieved using suture passer 200. More specifically, in order to retrieve the portion of suture "S," actuator 234 is depressed, moving shaft 232 to the extended position such that the portion of suture "S" may be once again positioned within the saddle of hooked distal end 236 of shaft 232, e.g., by manipulating suture passer 200 relative to the portion of suture "S" (see FIGS. 4A-4C). Thereafter, shaft 232 (FIGS. 4B-4C) is returned to the retracted position to retain the portion of suture "S" at the distal end of suture passer 200. Suture passer 200 is then withdrawn proximally through tissue and lumen 142*b* (FIGS. 2-3) of inner member 140, likewise translating the portion of suture "S" proximally through tissue on the opposite side of the opening in tissue as compared to the portion of suture "S" previously translated through tissue.

Figure 5F:
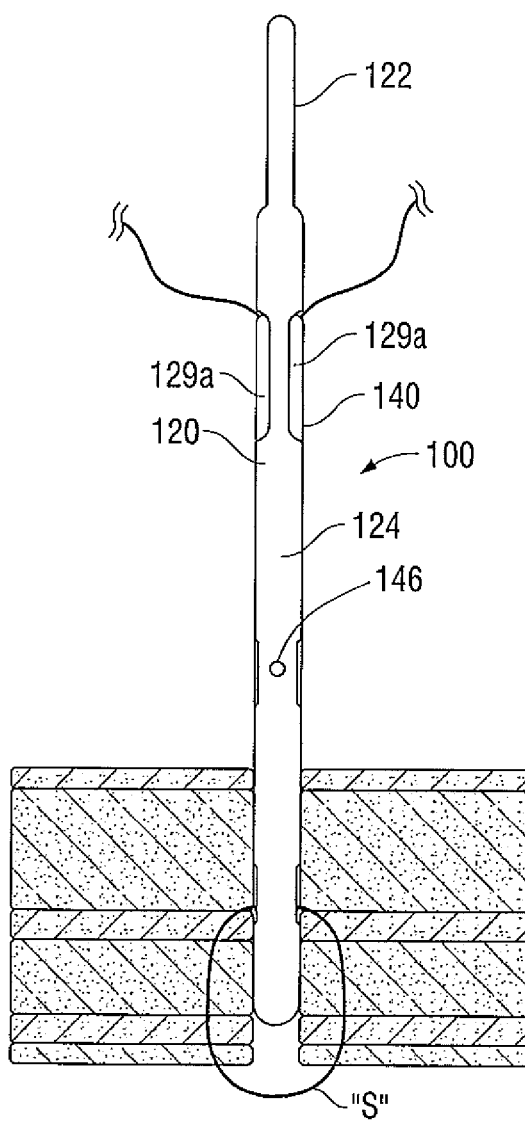
FIG. 5F is a side, perspective, partial cross-sectional view of the wound closure device of FIG. 1A positioned within the opening in tissue in the insertion/withdrawal position after depositing and retrieving the portion of suture.
Figure 5G:
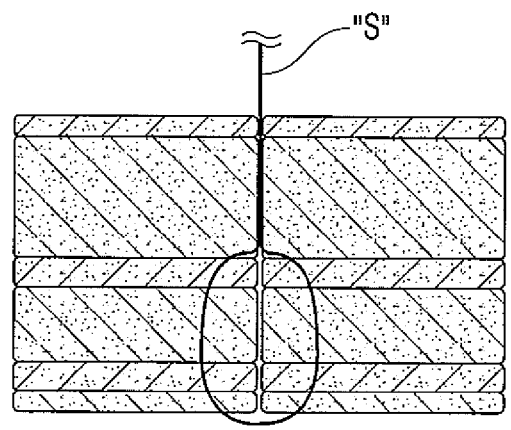
FIG. 5G is side, cross-sectional view illustrating the suture tied off to close the opening in tissue.

Referring to FIGS. 5F and 5G, once suture passer 200 has been proximally withdrawn from wound closure device 100, inner member 140 of wound closure device 140 is pivoted back to the insertion/withdrawal position and wound closure device 100 is withdrawn from the opening in tissue, leaving suture "S" defining a "U"-shaped configuration with portions of suture "S" extending through tissue on either side of the opening and across the opening on an internal side of tissue. With suture "S" in this position, suture "S" may be tied off to close the opening in tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A wound closure device, comprising:
an outer member defining a proximal end and a distal end;
an inner member at least partially disposed within the outer member and defining a proximal end and a distal end and first and second lumens extending longitudinally between the proximal end and the distal end on opposite sides of the inner member, the inner member configured for receipt of a suture passer therethrough, the inner member pivotably coupled to the outer member at an intermediate position between the proximal and distal ends of both the outer member and the inner member, the inner member pivotable relative to the outer member between a first position, wherein the inner member is coaxially disposed relative to the outer member, a second position, wherein the inner member is pivoted relative to the outer member such that the distal end of the inner member extends radially outwardly from the outer member in a first direction and such that the proximal end of the inner member extends radially outwardly from the outer member in a second, opposite direction, and a third position, wherein the inner member is pivoted relative to the outer member such that the distal end of the inner member extends radially outwardly from the outer member in the second direction and such that the proximal end of the inner member extends radially outwardly from the outer member in the first direction.

2. The wound closure device according to claim 1, wherein, in the first position, the inner member is disposed within an outer radial dimension of the outer member.

3. The wound closure device according to claim 1, wherein the outer member includes a handle portion disposed at the proximal end thereof, a distal cap disposed at the distal end thereof, and a body portion extending between the handle portion and distal cap.

4. The wound closure device according to claim 3, wherein the distal cap defines an atraumatic distal tip.

5. The wound closure device according to claim 3, wherein the handle portion is disposed within an outer radial dimension of at least one of the distal cap and the body portion.

6. The wound closure device according to claim 1, wherein the outer member includes a pair of opposed side walls configured to receive the inner member therebetween.

7. The wound closure device according to claim 6, further comprising a pivot pin pivotably coupling the side walls of the outer member to the inner member.

8. The wound closure device according to claim 6, wherein each side wall defines at least one cut-out configured to facilitate pivoting of the inner member relative to the outer member from the first position to at least one of the second and third positions.

9. The wound closure device according to claim 1, wherein the first lumen is configured to guide a suture passer through tissue when the inner member is disposed in the first deployed position and the second lumen is configured to guide a suture passer through tissue when the inner member is disposed in the second deployed position.

10. A method of closing an opening in tissue, comprising:
  positioning a wound closure device within an opening in tissue, the wound closure device including an outer member and an inner member at least partially disposed within the outer member and pivotably coupled to the outer member;
  pivoting the inner member relative to the outer member from a first position, wherein the inner member is coaxially disposed relative to the outer member, to a second position, wherein the inner member is pivoted relative to the outer member such that a distal end of the inner member extends in a first direction radially outwardly from the outer member adjacent tissue on a first side of the opening in tissue, and such that a proximal end of the inner member extends radially outwardly from the outer member in a second, opposite direction;
  inserting a suture passer longitudinally through the inner member, through tissue, and into an internal surgical site on the first side of the opening in tissue to at least one of deposit and retrieve a portion of a suture;
  withdrawing the suture passer proximally through tissue and the inner member;
  pivoting the inner member relative to the outer member from the second position to a third position, wherein the inner member is pivoted relative to the outer member such that the distal end of the inner member extends in the second direction radially outwardly from the outer member adjacent tissue on a second, opposite side of the opening in tissue, and such that the proximal end of the inner member extends radially outwardly from the outer member in the first, opposite direction;
  inserting the suture passer longitudinally through the inner member, through tissue, and into an internal surgical site on the second side of the opening in tissue to at least one of deposit and retrieve the portion of a suture; and
  withdrawing the suture passer proximally through tissue and the inner member.

11. The method according to claim 10, further comprising, initially:
  providing a surgical access assembly disposed within an opening in tissue;
  inserting the wound closure device through the surgical access assembly; and
  withdrawing the surgical access assembly from the opening in tissue, proximally about the wound closure device such that the wound closure device is left positioned within the opening in tissue.

12. The method according to claim 10, further comprising, before inserting the suture passer into the internal surgical site on the first side of the opening in tissue:
  engaging the portion of suture with the suture passer, wherein inserting the suture passer into the internal surgical site on the first side of the opening in tissue includes translating the portion of suture distally through the inner member and tissue into the internal surgical site; and
  depositing the portion of suture within the internal surgical site once the portion of suture is positioned within the internal surgical site.

13. The method according to claim 12, further comprising, after inserting the suture passer into the internal surgical site on the second side of the opening in tissue:
  engaging the portion of suture with the suture passer, wherein withdrawing the suture passer proximally through tissue on the second side of the opening in tissue includes withdrawing the portion of suture proximally though tissue and the inner member.

14. The method according to claim 13, further comprising tying off the suture to close the opening in tissue.

* * * * *